US006489309B1

(12) United States Patent
Singh et al.

(10) Patent No.: US 6,489,309 B1
(45) Date of Patent: *Dec. 3, 2002

(54) POLYSACCHARIDE CONJUGATES OF BIOMOLECULES

(75) Inventors: Rajendra Singh, San Jose; Harshvardhan Mehta, Fremont, both of CA (US)

(73) Assignee: Dade Behring Marburg GmbH, Marburg (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/314,055

(22) Filed: May 18, 1999

Related U.S. Application Data

(63) Continuation of application No. 08/907,842, filed on Aug. 8, 1997.

(51) Int. Cl.$^7$ .............................................. A01N 43/04
(52) U.S. Cl. ........................ 514/54; 514/59; 514/367; 536/51; 524/54
(58) Field of Search .............................. 536/51; 514/54, 514/59, 367; 524/54

(56) References Cited

U.S. PATENT DOCUMENTS

| 3,817,837 | A | 6/1974 | Rubenstein et al. |
| 3,996,345 | A | 12/1976 | Ullman et al. |
| RE29,169 | E | 4/1977 | Schuurs et al. |
| 4,098,876 | A | 7/1978 | Piasio et al. |
| 4,233,402 | A | 11/1980 | Maggio et al. |
| 4,244,940 | A | 1/1981 | Jeong et al. |
| 4,264,766 | A | 4/1981 | Fischer |
| 4,275,149 | A | 6/1981 | Litman et al. |
| 4,318,980 | A | 3/1982 | Boguslaski et al. |
| 4,374,925 | A | 2/1983 | Litman et al. |
| 4,391,904 | A | 7/1983 | Litman et al. |
| 4,474,878 | A | 10/1984 | Halbert et al. |
| 4,486,530 | A | 12/1984 | David et al. |
| 4,801,504 | A | 1/1989 | Burdick et al. |
| 4,857,453 | A | 8/1989 | Ullman et al. |
| 4,868,104 | A | 9/1989 | Kurn et al. |
| 4,959,303 | A | 9/1990 | Milburn et al. |
| 5,089,390 | A | 2/1992 | Davalian et al. |
| 5,185,243 | A | 2/1993 | Ullman et al. |
| 5,204,098 | A | 4/1993 | Szu et al. |
| 5,338,532 | A | 8/1994 | Tomalia et al. |
| 5,527,524 | A | 6/1996 | Tomalia et al. |
| 5,527,713 | A | 6/1996 | Bolton et al. |
| 5,554,386 | A | 9/1996 | Groman et al. |
| 5,554,730 | A | 9/1996 | Woiszwillo et al. |
| 5,561,049 | A | 10/1996 | Vold et al. |
| 5,627,078 | A | 5/1997 | Karl et al. |
| 5,651,971 | A | 7/1997 | Lees et al. |
| 5,707,877 | A | 1/1998 | Siiman et al. |
| 5,714,166 | A | 2/1998 | Tomalia et al. |
| 5,776,706 | A | 7/1998 | Siiman et al. |
| 5,840,674 | A | 11/1998 | Yatvin et al. |
| 5,849,301 | A | 12/1998 | Lees |
| 5,891,741 | A | 4/1999 | Siiman et al. |
| 5,929,049 | A | * 7/1999 | Singh et al. ................... 514/54 |

FOREIGN PATENT DOCUMENTS

EP 0 315 456 B1 6/1994

OTHER PUBLICATIONS

Lauritzen, et al., *Dot Immunobinding and Immunoblotting of Picogram and Nanogram Quantities of Small Peptides on Activated Nitrocellulose*, Journal of Immunological Methods, 131:257–267, 1990.

Margel, et al., *Novel Effective Immunoadsorbents Based on Agarose–Polyaldehyde Microsphere Beads: Synthesis and Affinity Chromatography*, Analytical Biochemistry: 128:342–350, 1983.

Wang, et al., *A Facile Synthesis of an Aldehydic Analog of Platelet Activating Factor and Its Use In The Production Of Specific Antibodies*, Chemistry and Physics of Lipids; 55:265–273, 1990.

Cuatrecasas, P., *Protein Purification by Affinity Chromatography*, Journal of Biological Chemistry., 245:3059–3065, 1970.

Yalow, et al., *Immunoassay of Endogenous Plasma Insulin in Man*, J. Clin. Invest. 39:1157–1175, 1960.

Dellacherie et al.; *A New Approach to Aldehydic Dextrans*; Polymer Bulletin, 31:145–149, 1993.

Callant, et al.; *A New Approach to Dextran Derivatives With Pendent Aldehyde Groups*, Reactive Polymers; 8:129–136; 1988.

Rogovin, et al., *Study of Synthesis Of Dextran Derivative*, J. Macromolecular Sci.–Chem., vol. 46 (3):569–593, 1972.

* cited by examiner

Primary Examiner—Ralph Gitomer
Assistant Examiner—Devesh Khare
(74) Attorney, Agent, or Firm—Patrick G. Gattari; Lois K. Ruszala

(57) ABSTRACT

Compounds that are modified polysaccharides having pendant aldehyde functionalities are disclosed. Each of the aldehyde functionalities is attached through a linker to a position corresponding to a hydrogen atom of a different hydroxyl group of unmodified polysaccharide. Also disclosed is a method for introducing an amine-reactive functionality into a dextran. The method comprises (a) reacting the dextran with an alkylating agent having a functionality that reacts with an hydroxyl group of the dextran thereby forming an alkylated dextran wherein the alkylating agent has an olefin group and (b) treating the alkylated dextran to convert the olefin group to an amine-reactive functionality. A polysaccharide can be conjugated to a biomolecule by carrying out the above method and reacting the amine-reactive functionality with an amine functionality on the biomolecule to produce polysaccharide conjugated to the biomolecule.

11 Claims, No Drawings

POLYSACCHARIDE CONJUGATES OF BIOMOLECULES

This application is a continuation of Application Ser. No. 08/907,842 filed Aug. 8, 1997.

BACKGROUND OF THE INVENTION

1. Field of the Invention

In the fields of medicine and clinical chemistry, many studies and determinations of physiologically reactive species such as cells, proteins, enzymes, cofactors, nucleic acids, substrates, antigens, antibodies, and so forth are carried out using conjugates involving specific binding pair members or labels or the like. Various assay techniques that involve the binding of specific binding pair members are known. These assay techniques generally also involve a label used in the detection part of the assay.

Polysaccharides, particularly dextran, have been conjugated to specific binding pair members to increase the stability of the specific binding pair member. Conjugation of these members to polysaccharides also increases the bulkiness of these molecules, which can enhance their effectiveness in assays involving specific binding pair members by interfering with binding to complementary specific binding pair members. Additionally, these conjugates, when present on a surface, permit specific binding of a complementary specific binding pair member to the surface with greatly reduced non-specific binding.

Aminodextran or carboxymethyldextran have usually been utilized for forming conjugates to specific binding pair members. Coupling the dextran to a protein, for example, can then be carried out through formation of an amide. However, aminodextrans and carboxymethyldextrans have a charge that often must be neutralized to control non-specific binding. Such neutralization is difficult to do without derivitizing the conjugate biomolecule at the same time.

An alternative method of conjugation is to first partially oxidize the polysaccharide with periodate to introduce aldehyde groups. Coupling to amine containing ligands and receptors can then be carried out by reductive amination. Although dextrans that are partially oxidized are not charged, the oxidation is difficult to precisely control, and the products have substantially reduced stability toward hydrolysis. A procedure for introducing aldehyde groups onto polysaccharides that does not compromise stability, is more readily carried out, and that permits ready conjugation, is therefore needed.

2. Description of the Related Art

Lauritzen, et al., discuss dot immunobinding and immunoblotting or picogram and nanogram quantities of small peptides on activated nitrocellulose in *Journal of Immunological Methods* (1990) 131:257–267.

Effective immunoadsorbents based on agarose-polyaldehyde microsphere beads: synthesis and affinity chromatography are disclosed by Margel, et al., *Analytical Biochemistry* (1983) 128:342–350.

U.S. Pat. No. 4,264,766 (Fischer) discloses immunological diagnostic reagents.

U.S. Pat. No. 4,801,504 (Burdick, et al.) discusses fluorescent labels having a polysaccharide bound to polymeric particles.

Polysaccharide-modified immunoglobulins having reduced immunogenic potential or improved pharmacokinetics is discussed in European Patent No. 0 315 456 B1.

Wang, et al., describe a facile synthesis of an aldehydic analog of platelet activating factor and its use in the production of specific antibodies in *Chemistry and Physics of Lipids* (1990) 55:265–273.

SUMMARY OF THE INVENTION

In one aspect, the present invention pertains to polymers comprising a sequence of repeating monosaccharide units, each of which is independently selected from monosaccharide units of the formula:

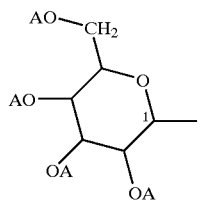

wherein one of the A's is a bond to the C1 glycosidic carbon of another of the units and the other A's are independently selected from the group consisting of H and QL, wherein L is a linking group linking O and Q and Q is C(Z)=D wherein D is O or $CR^1R^2$ wherein $R^1$ and $R^2$ are independently H, alkyl or aryl and Z is H or C(Y)=O wherein Y is $R^3$, $OR^3$ or $NR^3R^4$ wherein $R^3$ and $R^4$ are independently H, alkyl or aryl and wherein any of L, $R^1$, $R^2$, $R^3$ and $R^4$ may be taken together to form a ring with the proviso that at least two of the A's in the polymer are QL. Also included are compounds produced by reaction of the above polymer with a biomolecule such as a polypeptide.

Another aspect of the present invention is a compound comprising the structure:

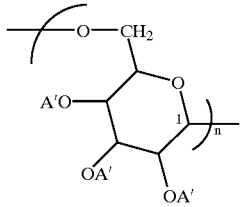

wherein n is 50 to 50,000, $A^1$ is independently selected from the group consisting of H and $Q^1L^1$, wherein $L^1$ is a linking group linking O and Q and $Q^1$ is C(Z)=D wherein D is O or $CR^1R^2$ wherein $R^1$ and $R^2$ are independently H, alkyl or aryl and Z is H or C(Y)=O wherein Y is $R^3$, $OR^3$ or $NR^3R^4$ wherein $R^3$ and $R^4$ are independently H, alkyl or aryl and wherein any of L, $R^1$, $R^2$, $R^3$ and $R^4$ may be taken together to form a ring with the proviso that at least two of the A's in the compound are $Q^1L^1$.

Also included are compounds produced by reaction of the above compound with a polypeptide.

Another aspect of the present invention is a compound that is a modified polysaccharide having pendant aldehyde functionalities wherein each of the aldehyde functionalities is attached through a linker to a position corresponding to a hydrogen atom of a different hydroxyl group of unmodified polysaccharide.

Another embodiment of the present invention is a method for introducing an amine-reactive functionality into a dextran. The method comprises reacting the dextran with an alkylating agent having a functionality that reacts with an hydroxyl group of the dextran thereby forming an alkylated dextran wherein the alkylating agent has an olefin group and treating the alkylated dextran to convert the olefin group to an amine-reactive functionality.

Another embodiment of the present invention is a method for conjugating a polysaccharide to a biomolecule such as a polypeptide. The polysaccharide is reacted with an alkylating agent having a functionality that reacts with a hydroxy group of the polysaccharide thereby forming an alkylated polysaccharide wherein the alkylating agent has an olefin group. The alkylated polysaccharide is treated to convert the olefin group to an amine-reactive functionality, which is reacted with an amine functionality on the biomolecule to produce polysaccharide conjugated to the biomolecule.

DESCRIPTION OF THE SPECIFIC EMBODIMENTS

The present invention provides a simple, inexpensive method for conjugation of a macromolecule to a polysaccharide for use in an immunoassay. Amine reactive functionalities such as an aldehyde are introduced into the polysaccharide for linking to a macromolecule. One advantage of the present invention is that, unlike prior methods, the number of amine reactive functionalities introduced into the polysaccharide can be controlled.

Before proceeding further with the description of the specific embodiments of the present invention, a number of terms will be defined.

Monosaccharide—a carbohydrate that cannot be hydrolyzed into simpler compounds such as an aldehyde alcohol or a ketone alcohol, e.g., a hexose or a pentose.

Polysaccharide—a carbohydrate containing three or more monosaccharide units; the polysaccharide can be hydrolyzed into the simpler monosaccharide units. Examples of polysaccharides by way of illustration and not limitation are dextran, starch, glycogen, polyribose and the like.

Dextran—a polysaccharide consisting of linear 1–6 linked (98%) glucose units; a polymerized glucose.

Alkyl—a monovalent branched or unbranched radical derived from an aliphatic hydrocarbon by removal of one H atom; includes both lower alkyl and upper alkyl.

Lower alkyl—alkyl containing from 1 to 5 carbon atoms such as, e.g., methyl, ethyl, propyl, butyl, isopropyl, isobutyl, pentyl, isopentyl, etc.

Upper alkyl—alkyl containing more than 6 carbon atoms, usually 6 to 20 carbon atoms, such as, e.g., hexyl, heptyl, octyl, etc.

Alkylidene—a divalent organic radical derived from an aliphatic hydrocarbon, such as, for example, ethylidene, in which 2 hydrogen atoms are taken from the same carbon atom.

Aryl—an organic radical derived from an aromatic hydrocarbon by the removal of one atom and containing one or more aromatic rings, usually one to four aromatic rings, such as, e.g., phenyl (from benzene), naphthyl (from naphthalene), etc., e.g., phenyl, naphthyl, phenanthryl.

Aralkyl—an organic radical having an alkyl group to which is attached an aryl group, e.g., benzyl, phenethyl, 3-phenylpropyl, 1-naphthylethyl, etc.

Alkoxy—an alkyl radical attached to the remainder of a molecule by an oxygen atom, e.g., methoxy, ethoxy, etc.

Aryloxy—an aryl radical attached to the remainder of a molecule by an oxygen atom, e.g., phenoxy, naphthoxy, etc., e.g., m-methoxyphenyl.

Aralkoxy—an aralkyl radical attached to the remainder of a molecule by an oxygen atom, e.g., benzoxy, 1-naphthylethoxy, etc.

Amine reactive functionality—a functionality reactive with an amine functionality, usually by virtue of nucleophilicity or basicity of the amine, such as, for example, an aldehyde, an α-keto carboxylic acid and the like.

Alkylating agent having a functionality that reacts with an hydroxyl group—a compound that has a functionality reactive with an hydroxyl group, usually by virtue of nucleophilicity of the neutral or ionized hydroxyl group, such as, for example, an oxiranyl radical, an alkyl radical comprising a leaving group such as, for example, halide (bromide, chloride, iodide); aryl sulfonates; alkyl sulfonates; aryl sulfates; alkyl sulfates; tosylates; acrylic acid derivatives such as acrylamide; vinyl sulfones; and the like.

Biomolecule—a polypeptide such as, for example, avidin, streptavidin, protein A, protein G, antibodies, and so forth.

Conjugate—a molecule comprised of two or more substructures bound together, generally through a linking group, to form a single structure.

Linking group—a portion of a structure which connects two or more substructures. The linking group may vary from a bond to a chain of from 1 to 30 or more atoms, usually from about 1 to 20 atoms, preferably 1 to 10 atoms, each independently selected from the group normally consisting of carbon, oxygen, sulfur, nitrogen, and phosphorous, usually carbon and oxygen. The number of heteroatoms in the linking group normally ranges from about 0 to 8, usually from about 1 to 6, more preferably 2 to 4. The number of atoms in the chain is determined by counting the number of atoms other than hydrogen or other monovalent atoms along the shortest route between the substructures being connected. The atoms of the linking group may be substituted with atoms other than hydrogen such as carbon, oxygen and so forth in the form, e.g., of alkyl, aryl, aralkyl, hydroxyl, alkoxy, aryloxy, aralkoxy, and the like. As a general rule, the length of a particular linking group can be selected arbitrarily to provide for convenience of synthesis with the proviso that there be minimal interference caused by the linking group with the ability of the present polymers to be attached to a biomolecule.

The linking group may be aliphatic or aromatic. When heteroatoms are present, oxygen will normally be present as oxy or oxo, bonded to carbon, sulfur, nitrogen or phosphorous; sulfur will be present as thioether or thiono; nitrogen will normally be present as nitro, nitroso or amino, normally bonded to carbon, oxygen, sulfur or phosphorous; phosphorous will be bonded to carbon, sulfur, oxygen or nitrogen, usually as phosphonate and phosphate mono- or diester. Functionalities present in the linking group may include esters, thioesters, amides, thioamides, ethers, ureas, thioureas, guanidines, azo groups, thioethers, carboxylate and so forth.

Examples, by way of illustration and not limitation, of various linking groups that find use in the present invention are found in U.S. Pat. No. 3,817,837, particularly at column 30, line 69, to column 36, line 10, which disclosure is incorporated herein by reference in its entirety.

Preferred linking groups include alkylene, i.e., $(CH_2)_p$ wherein p is an integer in the range of 1 to 10, preferably 1 to 5, wherein one or more hydrogens, usually one hydrogen, on one or more of the carbons, usually one, of the alkylenes may be substituted with $OR^9$ wherein $R^9$ is H, alkyl or aryl, e.g., methylene, ethylene, propylene, butylene, pentylene, hexylene, phenylene, p-benzylene and so forth; alkyleneoxyalkylene, i.e., $(CH_2)_qX(CH_2)_r$ wherein q and r are the same or different and are integers in the range of 1 to 5, preferably 1 to 3, and wherein one or more hydrogens, usually one hydrogen, on one or both, usually one, of the alkylenes may be substituted with $OR^9$ wherein $R^9$ is H, alkyl or aryl, preferably H, e.g., methyleneoxymethylene, methyleneoxyethylene, ethyleneoxyethylene, 1-methyleneoxy-2-hydroxyethylene and so forth and X is independently O or S, preferably O.

Member of a specific binding pair ("sbp member")—one of two different molecules, having an area on the surface or in a cavity which specifically binds to and is thereby defined as complementary with a particular spatial and polar organization of the other molecule. The members of the specific binding pair are referred to as ligand and receptor (antiligand). These will usually be members of an immunological pair such as antigen-antibody, although other specific binding pairs such as biotin-avidin, hormones-hormone receptors, nucleic acid duplexes, IgG-protein A, polynucleotide pairs such as DNA-DNA, DNA-RNA, and the like are not immunological pairs but are included in the definition of sbp member for the purpose of describing this invention.

Analyte—the compound or composition to be detected. The analyte can be comprised of a member of a specific binding pair (sbp) and may be a ligand, which is usually monovalent (monoepitopic), usually haptenic, and is a single compound or plurality of compounds which share at least one common epitopic or determinant site.

The monoepitopic ligand analytes will generally be from about 100 to 2,000 molecular weight, more usually from 125 to 1,000 molecular weight. The analytes include drugs, metabolites, pesticides, pollutants, and the like. Representative analytes, by way of example and not limitation, include (i) alkaloids such as morphine alkaloids, which include morphine, codeine, heroin, dextromethorphan, their derivatives and metabolites; cocaine alkaloids, which include cocaine and benzyl ecgonine, their derivatives and metabolites; ergot alkaloids, which include the diethylamide of lysergic acid; steroid alkaloids; iminazoyl alkaloids; quinazoline alkaloids; isoquinoline alkaloids; quinoline alkaloids, which include quinine and quinidine; diterpene alkaloids, their derivatives and metabolites; (ii) steroids, which include the estrogens, androgens, andreocortical steroids, bile acids, cardiotonic glycosides and aglycones, which includes digoxin and digoxigenin, saponins and sapogenins, their derivatives and metabolites; steroid mimetic substances, such as diethylstilbestrol; (iii) lactams having from 5 to 6 annular members, which include the barbiturates, e.g., Phenobarbital and secobarbital, diphenylhydantoin, primidone, ethosuximide, and their metabolites; (iv) aminoalkylbenzenes, with alkyl of from 2 to 3 carbon atoms, which include the amphetamines; catecholamines, which include ephedrine, L-dopa, epinephrine; narceine; papaverine; and metabolites of the above; (v) benzheterocyclics which include oxazepam, chlorpromazine, tegretol, their derivatives and metabolites, the heterocyclic rings being azepines, diazepines and phenothiazines; (vi) purines, which includes theophylline, caffeine, their metabolites and derivatives; (vii) drugs derived from marijuana, which include cannabinol and tetrahydrocannabinol; (viii) hormones such as thyroxine, cortisol, triiodothyronine, testosterone, estradiol, estrone, progesterone, polypeptides such as angiotensin, LHRH, and immunosuppressants such as cyclosporin, FK506, mycophenolic acid (MPA), and so forth; (ix) vitamins such as A, B, e.g. B12, C, D, E and K, folic acid, thiamine; (x) prostaglandins, which differ by the degree and sites of hydroxylation and unsaturation; (xi) tricyclic antidepressants, which include imipramine, dismethylimipramine, amitriptyline, nortriptyline, protriptyline, trimipramine, chlomipramine, doxepine, and desmethyldoxepin; (xii) anti-neoplastics, which include methotrexate; (xiii) antibiotics, which include penicillin, chloromycetin, actinomycetin, tetracycline, terramycin, the metabolites and derivatives; (xiv) nucleosides and nucleotides, which include ATP, NAD, FMN, adenosine, guanosine, thymidine, and cytidine with their appropriate sugar and phosphate substituentes; (xv) miscellaneous individual drugs which include methadone, meprobamate, serotonin, meperidine, lidocaine, procainamide, acetylprocainamide, propranolol, griseofulvin, valproic acid, butyrophenones, antihistamines, chloramphenicol, anticholinergic drugs, such as atropine, their metabolites and derivatives; (xvi) metabolites related to diseased states include spermine, galactose, phenylpyruvic acid, and porphyrin Type 1; (xvii) aminoglycosides, such as gentamicin, kanamicin, tobramycin, and amikacin; and (xviii) pesticides such as polyhalogenated biphenyls, phosphate esters, thiophosphates, carbamates, polyhalogenated sulfenamides, their metabolites and derivatives.

Polyvalent analytes are normally poly(amino acids), i.e., polypeptides and proteins, polysaccharides, nucleic acids, and combinations thereof. Such combinations include components of bacteria, viruses, chromosomes, genes, mitochondria, nuclei, cell membranes and the like. For the most part, the polyepitopic ligand analytes will have a molecular weight of at least about 5,000, more usually at least about 10,000. In the poly(amino acid) category, the poly(amino acids) of interest will generally be from about 5,000 to 5,000,000 molecular weight, more usually from about 20,000 to 1,000,000 molecular weight; among the hormones of interest, the molecular weights will usually range from about 5,000 to 60,000 molecular weight.

A wide variety of proteins may be considered as to the family of proteins having similar structural features, proteins having particular biological functions, proteins related to specific microorganisms, particularly disease causing microorganisms, etc. Such proteins include, for example, immunoglobulins, cytokines, enzymes, hormones, cancer antigens, nutritional markers, tissue specific antigens, etc. Such proteins include, by way of illustration and not limitation, protamines, histones, albumins, globulins, scleroproteins, phosphoproteins, mucoproteins, chromoproteins, lipoproteins, nucleoproteins, glycoproteins, T-cell receptors, proteoglycans, HLA, unclassified proteins, e.g., somatotropin, prolactin, insulin, pepsin, proteins found in human plasma, blood clotting factors, protein hormones such as, e.g., follicle-stimulating hormone, luteinizing hormone, luteotropin, prolactin, chorionic gonadotropin, tissue hormones, cytokines, cancer antigens such as, e.g., PSA, CEA, a-fetoprotein, acid phosphatase, CA19.9 and CA125, tissue specific antigens, such as, e.g., alkaline phosphatase, myoglobin, CPK-MB and calcitonin, and peptide hormones. Other polymeric materials of interest are mucopolysaccharides and polysaccharides.

For receptor analytes, the molecular weights will generally range from 10,000 to $2 \times 10^8$, more usually from 10,000 to $10^6$. For immunoglobulins, IgA, IgG, IgE and IgM, the molecular weights will generally vary from about 160,000 to about $10^6$. Enzymes will normally range from about 10,000 to 1,000,000 in molecular weight. Natural receptors vary widely, generally being at least about 25,000 molecular weight and may be $10^6$ or higher molecular weight, including such materials as avidin, DNA, RNA, thyroxine binding globulin, thyroxine binding prealbumin, transcortin, etc.

The term analyte further includes oligonucleotide and polynucleotide analytes such as m-RNA, r-RNA, t-RNA, DNA, DNA-RNA duplexes, etc.

The analyte may be a molecule found directly in a sample such as biological tissue, including body fluids, from a host.

The sample can be examined directly or may be pretreated to render the analyte more readily detectable by removing unwanted materials. The sample may be pretreated to separate or lyse cells; precipitate, hydrolyse or denature proteins; hydrolyze lipids; solubilize the analyte; or the like. Such pretreatment may include, without limitation: centrifugation; treatment of the sample with an organic solvent, for example, an alcohol, such as methanol; and treatment with detergents. The sample can be prepared in any convenient medium which does not interfere with an assay. An aqueous medium is preferred.

The analyte of interest may be determined by detecting an agent probative of the analyte of interest such as a specific binding pair member complementary to the analyte of interest, whose presence will be detected only when the analyte of interest is present in a sample. Thus, the agent probative of the analyte becomes the analyte that is detected in an assay.

The biological tissue includes excised tissue from an organ or other body part of a host and body fluids, for example, urine, whole blood, plasma, serum, saliva, semen, stool, sputum, cerebral spinal fluid, tears, mucus, and the like. Preferably, the sample is plasma or serum.

Polynucleotide—a compound or composition which is a polymeric nucleotide having in the natural state about 50 to 500,000 or more nucleotides and having in the isolated state about 15 to 50,000 or more nucleotides, usually about 15 to 20,000 nucleotides, more frequently 15 to 10,000 nucleotides. Polynucleotide includes nucleic acids from any source in purified or unpurified form, naturally occurring or synthetically produced, including DNA (dsDNA and ssDNA) and RNA, usually DNA, and may be t-RNA, m-RNA, r-RNA, mitochondrial DNA and RNA, chloroplast DNA and RNA, DNA-RNA hybrids, or mixtures thereof, genes, chromosomes, plasmids, the genomes of biological material such as microorganisms, e.g., bacteria, yeasts, viruses, viroids, molds, fungi, plants, animals, humans, and fragments thereof, and the like.

Ligand—any organic compound for which a receptor naturally exists or can be prepared.

Hapten—a compound capable of binding specifically to corresponding antibodies, but does not itself act as an immunogen (or antigen) for preparation of the antibodies. Antibodies which recognize a hapten can be prepared against compounds comprised of the hapten linked to an immunogenic (or antigenic) carrier. Haptens are a subset of ligands.

Ligand analog—a modified ligand, an organic radical or analyte analog, usually of a molecular weight greater than 100, which can compete with the analogous ligand for a receptor, the modification providing means to join a ligand analog to another molecule. The ligand analog will usually differ from the ligand by more than replacement of a hydrogen with a bond which links the ligand analog to a hub or label, but need not. The ligand analog can bind to the receptor in a manner similar to the ligand. The analog could be, for example, an antibody directed against the idiotype of an antibody to the ligand.

Receptor ("antiligand")—any compound or composition capable of recognizing a particular spatial and polar organization of a molecule, e.g., epitopic or determinant site. Illustrative receptors include naturally occurring receptors, e.g., thyroxine binding globulin, antibodies, enzymes, Fab fragments, lectins, nucleic acids, protein A, complement component C1q, and the like.

Specific binding—the specific recognition of one of two different molecules for the other compared to substantially less recognition of other molecules. Generally, the molecules have areas on their surfaces or in cavities, also referred to as "binding sites," giving rise to specific recognition between the two molecules. Exemplary of specific binding are antibody-antigen interactions, enzyme-substrate interactions, polynucleotide interactions, and so forth.

Non-specific binding—non-covalent binding between molecules that is relatively independent of specific surface structures. Non-specific binding may result from several factors including hydrophobic interactions between molecules.

Antibody—an immunoglobulin which specifically binds to and is thereby defined as complementary with a particular spatial and polar organization of another molecule. The antibody can be monoclonal or polyclonal and can be prepared by techniques that are well known in the art such as immunization of a host and collection of sera (polyclonal) or by preparing continuous hybrid cell lines and collecting the secreted protein (monoclonal), or by cloning and expressing nucleotide sequences or mutagenized versions thereof coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and $F(ab')_2$, Fab', and the like. In addition, aggregates, polymers, and conjugates of immunoglobulins or their fragments can be used where appropriate so long as binding affinity for a particular molecule is maintained.

Substituted—means that a hydrogen atom of a molecule has been replaced by another atom, which may be a single atom such as a halogen, etc., or part of a group of atoms forming a functionality as described above. Such substituent may be a group or functionality imparting hydrophilicity or lipophilicity. Hydrophilicity may be achieved by a functional group having one or more atoms such as oxygen, nitrogen, sulfur, phosphorus, and so forth; such groups include sulfonate, sulfate, phosphate, amidine, phosphonate, carboxylate, hydroxyl particularly polyols, amine, ether, amide, and the like. Illustrative functional groups are carboxyalkyl, sulfonoxyalkyl, $CONHOCH_2COOH$, CO-(glucosamine), sugars, dextran, cyclodextrin, $SO_2NHCH_2COOH$, $SO_3H$, $CONHCH_2CH_2SO_3H$, $PO_3H_2$, $OPO_3H_2$, hydroxyl, carboxyl, ketone, and combinations thereof. Lipophilicity may be achieved by a functional group such as carbon atoms substituted with hydrogen or halogen and can include alkyl, alkylidene, aryl and aralkyl. The lipophilic group or functionality will normally have one to six straight or branched chain aliphatic groups of at least 6 carbon atoms, more usually at least 10 carbon atoms, and preferably at least 12 carbon atoms, usually not more than 30 carbon atoms.

Support or surface—a solid phase, typically a support or surface, which is a porous or non-porous water insoluble material that can have any one of a number of shapes, such as strip, rod, plate, well, particle or bead. A wide variety of suitable supports are disclosed in Ullman, et al., U.S. Pat. No. 5,185,243, columns 10–11, Kurn, et al., U.S. Pat. No. 4,868,104, column 6, lines 21–42, and Milburn, et al., U.S. Pat. No. 4,959,303, column 6, lines 14–31, which are incorporated herein by reference.

The surface can be hydrophilic or capable of being rendered hydrophilic and includes inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly(4-methylbutene), polystyrene, polymethacrylate, poly(ethylene terephthalate), nylon, poly (vinyl butyrate), etc.; either used by themselves or in conjunction with other materials; glass available as Bioglass, ceramics, metals, and the like. Natural or synthetic assemblies such as liposomes, phospholipid vesicles, and cells can also be employed.

Binding of sbp members to a support or surface, other than by use of the compounds of the present invention, may be accomplished by well-known techniques, commonly available in the literature. See, for example, "Immobilized Enzymes," Ichiro Chibata, Halsted Press, New York (1978) and Cuatrecasas, *J. Biol. Chem.*, 245:3059 (1970).

Signal producing system ("sps")—one or more components, at least one component being a detectable label, which generate a detectable signal that relates to the amount of bound and/or unbound label, i.e. the amount of label bound or not bound to the compound being detected. The label is any molecule that produces or can be induced to produce a signal, and may be, for example, a fluorescer, radio-label, enzyme, chemiluminescer or photosensitizer. Thus, the signal is detected and/or measured by detecting enzyme activity, luminescence, light absorbance or radioactivity as the case may be.

Suitable labels include, by way of illustration and not limitation, enzymes such as alkaline phosphatase, glucose-6-phosphate dehydrogenase ("G6PDH") and horseradish peroxidase; ribozyme; a substrate for a replicase such as QB replicase; promoters; dyes; fluorescers, such as fluorescein, isothiocyanate, rhodamine compounds, phycoerythrin, phycocyanin, allophycocyanin, o-phthaldehyde, and fluorescamine; chemiluminescers such as isoluminol; sensitizers; coenzymes; enzyme substrates; radiolabels such as $^{125}$I, $^{131}$I, $^{14}$C, $^{3}$H, $^{57}$Co and $^{75}$Se; particles such as latex or carbon particles; metal sol; crystallite; liposomes; cells, etc., which may be further labeled with a dye, catalyst or other detectable group. Suitable enzymes and coenzymes are disclosed in Litman, et al., U.S. Pat. No. 4,275,149, columns 19–28, and Boguslaski, et al., U.S. Pat. No. 4,318,980, columns 10–14; suitable fluorescers and chemiluminescers are disclosed in Litman, et al., U.S. Pat. No. 4,275,149, at columns 30 and 31; which are incorporated herein by reference.

There are numerous methods by which the label can produce a signal detectable by external means, desirably by visual examination, for example, by electromagnetic radiation, heat, and chemical reagents. The label or other sps members can also be bound to an sbp member, another molecule or to a support.

Labels include groups detectable by means of electromagnetic radiation or by electrochemical detection including dyes, fluorescers, chemiluminescers, and radioactive isotopes.

The label can directly produce a signal and, therefore, additional components are not required to produce a signal. Numerous organic molecules, for example fluorescers, are able to absorb ultraviolet and visible light, where the light absorption transfers energy to these molecules and elevates them to an excited energy state. This absorbed energy is then dissipated by emission of light at a second wavelength. Other labels that directly produce a signal include radioactive isotopes and dyes.

Alternately, the label may need other components to produce a signal, and the signal producing system would then include all the components required to produce a measurable signal, which may include substrates, coenzymes, enhancers, additional enzymes, substances that react with enzymic products, catalysts, activators, cofactors, inhibitors, scavengers, metal ions, and a specific binding substance required for binding of signal generating substances. A detailed discussion of suitable signal producing systems can be found in Ullman, et al., U.S. Pat. No. 5,185,243, columns 11–13, incorporated herein by reference.

The label and/or other sps member may be bound to an sbp member or to a support utilizing the compounds and compositions of the present invention. Alternatively, the label can be bound covalently to an sbp member such as, for example, an antibody; a receptor for an antibody, a receptor that is capable of binding to a small molecule conjugated to an antibody, or a ligand analog. Bonding of the label to the sbp member may be accomplished by chemical reactions that result in replacing a hydrogen atom of the label with a bond to the sbp member or may include a linking group between the label and the sbp member. Other sps members may also be bound covalently to sbp members. For example, two sps members such as a fluorescer and quencher can each be bound to a different antibody that forms a specific complex with the analyte. Formation of the complex brings the fluorescer and quencher in close proximity, thus permitting the quencher to interact with the fluorescer to produce a signal. Methods of conjugation are well known in the art. See, for example, Rubenstein, et al., U.S. Pat. No. 3,817,837, incorporated herein by reference.

Assay—method for the determination of the presence or amount of an analyte.

Measuring the amount of an analyte—quantitative, semiquantitative, and qualitative methods as well as all other methods for determining an analyte are considered to be methods of measuring the amount of an analyte. For example, a method which merely detects the presence or absence of an analyte in a sample suspected of containing the analyte is considered to be included within the scope of the present invention. The terms "detecting" and "determining," as well as other common synonyms for measuring, are contemplated within the scope of the present invention.

Ancillary Materials—Various ancillary materials will frequently be employed in the assay in accordance with the present invention. For example, buffers will normally be present in the assay medium, as well as stabilizers for the assay medium and the assay components. Frequently, in addition to these additives, proteins may be included, such as albumins; organic solvents such as formamide; quaternary ammonium salts; polyanions such as dextran sulfate; surfactants, particularly non-ionic surfactants; binding enhancers, e.g., polyalkylene glycols; or the like.

Wholly or partially sequentially—when various agents are combined other than concomitantly (simultaneously), one or more may be combined with one or more of the remaining agents to form a subcombination.

In one aspect the present invention pertains to polymers comprising a sequence of repeating monosaccharide units, each of which is independently selected from monosaccharide units of the formula:

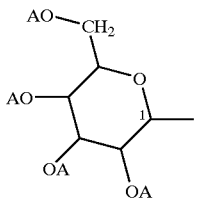

wherein one of the A's is a bond to the C1 glycosidic carbon (as indicated in the above formula) of another of the units and the other A's are independently selected from the group consisting of H and QL, wherein L is a linking group linking O and Q and Q is C(Z)=D wherein D is O or $CR^1R^2$ wherein $R^1$ and $R^2$ are independently H, alkyl or aryl and Z is H or C(Y)=O wherein Y is $R^3$, $OR^3$ or $NR^3R^4$ wherein $R^3$ and $R^4$ are independently H, alkyl or aryl and wherein any of L, $R^1$, $R^2$, $R^3$ and $R^4$ may be taken together to form a ring with the proviso that at least two of the A's in the polymer are QL. Usually, a ring, when present, is a three to eight member ring, preferably, a five to seven member ring, that can have one or more unsaturations. The ring may be aryl or aralkyl. One or more atoms of the ring may be substituted with a substituent other than hydrogen to form one or more functionalities. The atoms of the ring other than hydrogen are usually carbon but may also include oxygen, sulfur, boron, silicon and/or nitrogen. Exemplary of such rings are benzene, naphthalene, anthracene, phenanthrene, pyridine, pyrimidine furan, indene, indane, pyrrole, thiophene, imidazole, and the like.

The above polymer generally has from about 3 to 50,000, preferably 25 to 10,000, more preferably 50 to 1,000 repeating monosaccharide units. Preferably, there are at least two A's in QL in at least one of the monosaccharide units for every 20, more preferably, every 10, monosaccharide units of the polymer.

The following are examples, by way of illustration and not limitation, of polymers in accordance with the present invention.

L is alkylene, e.g., methylene (—$CH_2$—), ethylene (—$CH_2CH_2$—), etc.; or alkyleneoxyhydroxyalkylene, e.g., 1-methyleneoxy-2-hydroxyethylene (—$CH_2$—O—$CH_2$—C(OH)H—), etc.

Q is (i) —CH=O, (ii) —C(O)—C(O)—$R^3$, (iii) —C(O)—C(O)—$OR^3$, (iv) —C(O)—C(O)—$NR^3$ $R^4$, (v) —CH=$CR^1R^2$, (vi) ($R^1R^2$)C=C—C(O)—$R^3$, (vii) ($R^1R^2$)C=C—C(O)—$OR^3$, and (viii) ($R^1R^2$)C=C—C(O)—$NR^3R^4$.

$R^3$ and $R^4$ are lower alkyl, preferably methyl.

Particularly preferred polymers in accordance with the present invention are those wherein the polymer is a modified dextran in which the A on the methyleneoxy oxygen of one of the units of the polymer is a bond to the C1 glycosidic carbon of another of the units of the polymer and QL is HC(O)$CH_2$— or HC(O)$CH_2OCH_2$C(OH)$HCH_2$—.

The polymers of the invention can be prepared in a number of ways. The following discussion of one example of a preparation of the above polymers is by way of illustration and not limitation. The method described below is readily carried out and does not compromise the stability of the polysaccharide. The method comprises reacting the polysaccharide with an alkylating agent having a functionality that reacts with an hydroxyl group of the polysaccharide thereby forming an alkylated polysaccharide wherein the alkylating agent has an olefin group and then treating the alkylated polysaccharide to convert the olefin group to an amine-reactive functionality.

The alkylating agent may comprise the structure

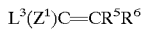

wherein $L^3$ is a group comprising a functionality reactive with a hydroxyl group of the polysaccharide, $R^5$ and $R^6$ are independently H, alkyl, aryl or may be taken together with each other or with $L^3$ to form a ring and $Z^1$ is H or C(W)=O wherein W is $R^7$, $OR^7$, or $NR^7R^8$ wherein $R^7$ and $R^8$ are independently H, alkyl or aryl. Usually, a ring, when present, is a three to eight member ring, preferably, a five to seven member ring, that can have one or more unsaturations. The ring may be aryl or aralkyl. One or more atoms of the ring may be substituted with a substituent other than hydrogen to form one or more functionalities. The atoms of the ring other than hydrogen are usually carbon but may also include oxygen, sulfur, boron, silicon and/or nitrogen. Exemplary of such rings are benzene, naphthalene, anthracene, phenanthrene, pyridine, pyrimidine furan, indene, indane, pyrrole, thiophene, imidazole, and the like.

The polymer that is desired will determine the particular alkylating agent to be used. For example, to make the polymer described above wherein QL is HC(O)$CH_2$—, one utilizes an alkylating agent wherein $L^3$ is methylene having a leaving group such as bromide, $Z^1$, $R^5$ and $R^6$ are H. To make the polymer described above wherein QL is HC(O)$CH_2OCH_2$C(OH)$HCH_2$—, one utilizes an alkylating agent wherein $L^3$ is $CH_2OCH_2(C_2H_3O)$ wherein $(C_2H_3O)$ is an oxiranyl radical. The latter alkylating agent is preferred when a water soluble polymer is desirable. Maintenance of the water solubility of the dextran can be achieved generally by incorporating a group that imparts hydrophilicity into the dextran during the introduction of the aldehyde group. Accordingly, a preferred alkylating agent is $CH_2$=CH$CH_2OCH_2(C_2H_3O)$, which results in the introduction of a QL that contains additional oxygen atoms, i.e., HC(O)$CH_2OCH_2$C(OH)$HCH_2$—.

For example, dextran is treated with allyl glycidyl ether ($CH_2$=CH$CH_2OCH_2(C_2H_3O)$) in an acidic aqueous medium. An acid catalyzed opening of the epoxide ring is employed, which results in the addition of a hydroxyl group at one of the carbon atoms of the dextran to one of the two carbon atoms of the epoxide ring to give allyloxydextran. For this step the pH of the medium is about 1 to 4, preferably 1.5 to 2.5. Usually, it is desirable to conduct the reaction in the presence of a Lewis acid such as, for example, $Zn(BF_4)_2$, $H_2SO_4$, $SnCl_2$, and the like. Accordingly, the pH for the reaction should not be so low or so high as to affect linkages in, or cause other deleterious effects on, the dextran molecule. Where a Lewis acid is employed, the pH should not be so high as to result in a deleterious effect on the Lewis acid such as causing precipitation of unwanted reaction materials. The amount of the Lewis acid employed is about 10–30% (weight/weight) of dextran. Control of the pH permits control of the number of aldehyde groups introduced into the dextran; thus pH control is important.

The time period for the reaction is usually about 6 to 18, preferably, about 10 to 15, hours. It is preferable to conduct the reaction in an atmosphere of inert gas, such as, for example, argon, neon, nitrogen and the like. The temperature of the reaction mixture is generally about 70 to 90° C., usually about 75 to 85° C., preferably, about 80° C.

The order of addition for the reagents usually involves dissolving the dextran, Lewis acid and alkylating agent such as allyl glycidyl ether in water with heating at about 60 to 80° C., preferably about 68 to 72° C. After the desired period of time, the reaction mixture is cooled and the resulting allyloxy dextran product is purified, for example, by filtration, ultrafiltration or the like.

The above procedure introduces on the average about one allyloxy group per 5 to 20, usually, 7 to 12, preferably, 8 to 10, polysaccharide units of the dextran molecule. Usually, only one allyloxy group is introduced into a polysaccharide unit that is alkylated, generally, at the hydroxyl group at the 2, 3 or 4 position.

The allyloxy dextran is treated to introduce an aldehyde functionality. To this end the double bond is oxidized by suitable means to cleave the double bond and introduce a terminal aldehyde group. The oxidation can be carried out by any means that produces a terminal aldehyde group but does not affect other parts of the dextran molecule. One convenient way to oxidize the double bond of the allyloxy dextran is to subject the allyloxy dextran to ozonolysis followed by reductive workup such as with dimethyl sulfide. To this end ozone is generated in the reaction mixture at a temperature of about 15 to 30° C., usually about 20 to 28° C., preferably, about 24 to 27° C. For this step the pH of the medium is about 5 to 8, preferably, 6 to 7. The amount of ozone used is generally that amount sufficient to oxidize all of the allyl groups to aldehydes. The time period for the reaction is usually about 5 to 10 hours, preferably, about 5 to 7 hours. It is preferable to conduct the reaction in atmosphere of inert gas. After the desired period of time, the reaction mixture is cooled and ozonide is reduced, for example, by the addition of a reducing agent such as, for example, a sulfide, thiosubstituted phosphine or the like. The resulting dextran aldehyde product is purified by precipitation with an organic solvent, dialysis or the like.

As an alternative to the above method for preparing the present polymers, the above alkylating agent can be replaced by $CH(O)CH_2OCH_2(C_2H_3O)$. The resulting product from this alkylating agent is the desired dextran aldehyde. Accordingly, the desired dextran aldehyde can be obtained by direct alkylation although the aforementioned alkylating agent is preferred because the free aldehyde undergoes side reactions under the acidic conditions.

In an alternate embodiment the amine-reactive functionality introduced is an alpha-keto carboxylic acid functionality. Again, the polymer that is desired will determine the particular alkylating agent to be used. For example, to make the polymer described above wherein QL is $HC(O)CH_2OCH_2C(OH)HCH_2$—, one can utilize an alkylating agent wherein $L^3$ is $CH_2OCH_2(C_2H_3O)$ wherein $(C_2H_3O)$ is an oxiranyl radical and $Z^1$ is $C(O)OH$. For example, dextran is treated with an alkylating agent of the formula $CH_2=C(COOH)CH_2OCH_2(C_2H_3O)$ in an acidic aqueous medium. As described above, an acid catalyzed opening of the epoxide ring is realized, which results in the addition of a hydroxyl group of the dextran to a carbon atom of the epoxide ring to give allyloxydextran. For this step the pH of the medium is about 1 to 4, preferably 1.5 to 2.5. Usually, it is desirable to conduct the reaction in the presence of a Lewis acid under conditions similar to those described above. After the desired period of time, the reaction mixture is cooled and the resulting product is purified by filtration, ultrafiltration or the like. The product is treated to introduce an aldehyde functionality. To this end the double bond is oxidized by suitable means to cleave the double bond and introduce an oxo functionality to yield an alpha keto acid product. The oxidation can be carried out by any means that produces an oxo functionality but does not affect other parts of the molecule. One convenient way to oxidize the double bond of this product to introduce an oxo functionality is to subject the product to ozonolysis as described above. The resulting alpha keto acid product is purified by filtration, ultrafiltration or the like.

As an alternative to the above method for preparing the present polymers, the above mentioned alkylating agent can be replaced by $C(O)(COOH)CH_2OCH_2(C_2H_3O)$. The direct product from this alkylating agent is the alpha keto acid substituted dextran.

In another exemplary approach in accordance with the present invention, a dextran aldehyde polymer can be prepared wherein QL is $HC(O)CH_2$—. In this approach an alkylating agent containing a leaving group, such as, for example, allyl bromide, is employed. The reaction comprises displacement of bromide of the alkylating agent by an oxygen atom of a polysaccharide unit of the dextran in the presence of a base such as sodium hydroxide, potassium hydroxide, or the like. Dextran is combined with allyl bromide in an aqueous medium in an inert atmosphere in the presence of a sufficient amount of a base to achieve the above mentioned displacement. For this step the pH of the medium is about 10 to 14, preferably 11 to 14. The pH for the reaction should not be so low or so high as to affect linkages in, or cause other deleterious effects on, the dextran molecule. Control of the pH permits control of the number of aldehyde groups introduced into the dextran; thus pH control is important.

The time period for the reaction is usually about 2 to 8 hours, preferably, about 3 to 5 hours. It is preferable to conduct the reaction in an atmosphere of inert gas.

The order of addition for the reagents is not critical. Preferably, the dextran is dissolved in water with heating at about 50 to 80° C., preferably about 60 to 70° C. Then, the pH of the medium is adjusted to the desired level. Next, the allyl bromide is added to the reaction mixture and the temperature is raised to the desired reaction temperature if necessary. After the desired period of time, the reaction mixture is cooled and the resulting allyloxy dextran product is purified by precipitation with an organic solvent, ultrafiltration or the like.

The above procedure introduces on the average about one allyl group per 3 to 20, usually 7 to 15, preferably, 8 to 12, polysaccharide units of the dextran molecule.

The allyl dextran is treated to introduce an aldehyde functionality as described above for the allyloxy dextran. The resulting dextran aldehyde product is purified by precipitation with an organic solvent, ultrafiltration or the like, as described previously.

Another aspect of the present invention is a method of conjugating the present polymers to a biomolecule such as a polypeptide. A polysaccharide is reacted with an alkylating agent having a functionality that reacts with a hydroxy group of the polysaccharide thereby forming an alkylated polysaccharide as described above. The alkylated polysaccharide is treated to yield an amine-reactive functionality as described above. The polysaccharide having an amine-reactive functionality is reacted with an amine functionality on the biomolecule to produce polymer conjugated to the biomolecule. The reaction conditions for achieving this reaction are dependent somewhat on the nature of the amine-reactive functionality. For example, a polysaccharide having an aldehyde functionality is reacted with an amine of the biomolecule. Generally, this reaction is carried out under mildly acidic conditions in the presence of a reducing agent such as cyanoborohydride or the like. The pH of the reaction medium containing the reactants should be low enough to permit an appreciable number of the amine groups to be protonated but not so low as to result in an insufficient amount of the free amine compounds. The pH is usually about 4 to 6, preferably 5.0 to 5.5. The time period for the reaction is usually about 10 to 20 hours, preferably, about 14 to 18. The temperature of the reaction mixture is generally about 15 to 30° C., usually, about 20 to 25° C. It is often desirable to block any aldehyde functionalities that have not reacted with polypeptide. To this end the conjugate produced above is treated with a suitable blocking reagent that will form a stable product with the remaining free aldehyde groups. Such a blocking agent can be, for example, hydroxyl amine, semicarbazide, phenylhydrazine, hydrazine, sodium cyanide and the like, preferably, hydroxyl amine. The resulting product is purified by conventional means such as, for example, ultrafiltration, precipitation, dialysis and so forth.

The polysaccharide compounds of the present invention conjugated to a polypeptide can be utilized in assays for analytes. The assay methods usually involve a sample suspected of containing an analyte, which is combined in an assay medium with reagents for carrying out the assay. Such reagents can include a binding partner for the analyte, analyte analogs, solid surfaces to which one of the above reagents is bound, binding partners for sbp members. One or more of the reagents can be labeled. The reagents are chosen such that a signal is obtained from a label in relation to the presence or amount of analyte in the sample. The assay can be performed either without separation (homogeneous) or with separation (heterogeneous) of any of the assay compounds or products.

Homogeneous immunoassays are exemplified by the EMIT® assay products (Syva Company, San Jose, Calif.) disclosed in Rubenstein, et al., U.S. Pat. No. 3,817,837, column 3, line 6 to column 6, line 64; immunofluorescence methods such as those disclosed in Ullman, et al., U.S. Pat. No. 3,996,345, column 17, line 59 to column 23, line 25; enzyme channeling techniques such as those disclosed in Maggio, et al., U.S. Pat. No. 4,233,402, column 6, line 25 to column 9, line 63; and other enzyme immunoassays such as the enzyme linked immunosorbant assay ("ELISA") are discussed in Maggio, E. T., infra. Exemplary of heterogeneous assays are the radioimmunoassay, disclosed in Yalow, et al., *J. Clin. Invest*. 39:1157 (1960). The above disclosures are all incorporated herein by reference. Another method to which the present invention has application is disclosed in Ullman, et al., U.S. Pat. No. 4,857,453, column 11, line 21 to column 14, line 42, and column 18, line 21 to column 21, line 55, incorporated herein by reference.

Heterogeneous assays usually involve one or more separation steps and can be competitive or non-competitive. A variety of competitive and non-competitive heterogeneous assay formats are disclosed in Davalian, et al., U.S. Pat. No. 5,089,390, column 14, line 25 to column 15, line 9, incorporated herein by reference. In a typical competitive heterogeneous assay a support having an antibody for analyte bound thereto is contacted with a medium containing the sample and analyte analog conjugated to a detectable label such as an enzyme (the "conjugate"). Analyte in the sample competes with the conjugate for binding to the antibody. After separating the support and the medium, the label activity of the support or the medium is determined by conventional techniques and is related to the amount of analyte in the sample.

A typical non-competitive sandwich assay is an assay disclosed in David, et al., U.S. Pat. No. 4,486,530, column 8, line 6 to column 15, line 63, incorporated herein by reference. In this method, an immune sandwich complex is formed in an assay medium. The complex comprises the analyte, a first antibody (monoclonal or polyclonal) that binds to the analyte and a second antibody that binds to the analyte or a complex of the analyte and the first antibody. Subsequently, the immune sandwich complex is detected and is related to the amount of analyte in the sample. The immune sandwich complex is detected by virtue of the presence in the complex of a label wherein either or both the first antibody and the second antibody contain labels or substituents capable of combining with labels.

Sandwich assays find use for the most part in the detection of antigen and receptor analytes. In the assay the analyte is bound by two antibodies specific for the analyte and, thus, the assay is also referred to as the two-site immunometric assay. In one approach a first incubation of unlabeled antibody coupled to a support, otherwise known as the insolubilized antibody, is contacted with a medium containing a sample suspected of containing the analyte. After a wash and separation step, the support is contacted with a medium containing the second antibody, which generally contains a label, for a second incubation period. The support is again washed and separated from the medium and either the medium or the support is examined for the presence of label. The presence and amount of label is related to the presence or amount of the analyte. For a more detailed discussion of this approach see U.S. Pat. Nos. Re 29,169 and 4,474,878, the relevant disclosures of which are incorporated herein by reference.

In a variation of the above sandwich assay the sample in a suitable medium is contacted with labeled antibody for the analyte and incubated for a period of time. Then, the medium is contacted with a support to which is bound a second antibody for the analyte. After an incubation period, the support is separated from the medium and washed to remove unbound reagents. The support or the medium is examined for the presence of the label, which is related to the presence or amount of analyte. For a more detailed discussion of this approach see U.S. Pat. No. 4,098,876, the relevant disclosure of which is incorporated herein by reference.

In another variation of the above, the sample, the first antibody bound to a support and the labeled antibody are combined in a medium and incubated in a single incubation step. Separation, wash steps and examination for label are as described above. For a more detailed discussion of this approach see U.S. Pat. No. 4,244,940, the relevant disclosure of which is incorporated herein by reference.

The present invention has application to all of the above assays. A particular example of an assay in accordance with the present invention is described below by way of illustration and not limitation. The assay is for the detection of an antibody in a sample suspected of containing such antibody and is described in more detail in U.S. patent application Ser. No. 08/310,028 filed Sep. 21, 1994, the disclosure of which is incorporated herein by reference. In the method an aqueous assay medium is formed comprising the sample, an antigen that binds the antibody thus forming an antigen:antibody complex, and a first binding agent that binds the complex and does not bind the antigen when the antigen is not part of the complex. The amount of antigen added to the medium is Z, wherein Z is within the range of X to nX and Z is less than Y, where n is 5–1000, preferably 10–100, X is the minimum amount of antigen that can be reliably detected when there are no antibodies present in a sample and Y is the maximum expected amount of antibodies in the sample. A second binding agent that selectively binds the antigen relative to binding the complex when the complex is bound to the first binding agent is combined with the assay medium. The antigen bound to the second binding agent is detected. The presence or amount thereof is related to the presence or amount of the antibodies in the sample.

A critical feature of the above method is that the first binding agent can bind the antigen:antibody complex in a manner that precludes binding of the second binding agent to the complex. The binding agents are sbp members and binding of the second binding agent to the first binding agent-bound complex can be better prevented when the first binding agent is bound to a soluble polymer or suspendable solid phase. This provides the added advantage that the first binding agent-bound complex does not need to be separated from the medium prior to the addition of the second binding agent because the first binding agent-bound complex does not interfere with the measurement of free antigen.

The sbp member that makes up the first binding agent is selected so that it binds the antigen:antibody complex and does not bind the antigen when the antigen is not part of the complex, i.e., the first binding agent does not significantly bind to any free or unbound antigen present in the medium. The sbp member may also bind other substances present in the sample, e.g., non-analyte antibodies. This is acceptable provided that the first binding agent does not bind antigen except when the antigen is bound to the analyte antibody.

Suitable sbp members for the first binding agents include, without limitation, antibodies to immunoglobulins; complement factor, C1q; rheumatoid factor; protein G and/or protein A. Some of these materials non-selectively bind immunoglobulins, for example, anti-Fab antibodies and protein A, some selectively bind relatively specific immunoglobulins such as anti-Fc antibodies and rheumatoid factor and some selectively bind immune complexes, for example, C1q. As noted above, in order to prevent binding of the second binding agent to the antigen:antibody complex, it is preferable to have the first binding agent further comprised of a suspendable solid phase or soluble polymer, i.e., the binding agent is bound to a suspendable solid phase or soluble polymer. In accordance with the present invention one of the above first binding agents, e.g., protein A, is conjugated to dextran aldehyde as described above and the conjugate is employed in the assay as described above.

The second binding agent is an sbp member that is capable of binding the antigen. It can be an antibody, preferably a monoclonal antibody, or other receptor for the antigen; a ligand to which the antigen binds as for example an irreversible inhibitor if the antigen is an enzyme; or one member of an sbp where the other member is bound to the antigen. Where the second binding agent is a polypeptide, e.g., an antibody, it can be conjugated with the dextran aldehyde of the present invention to form a soluble polymer.

After addition of the second binding agent, the antigen bound to the second binding agent is detected, its presence or amount being related to the presence or amount of the antibodies in the sample. This relationship is inversely proportional since the higher the concentration of antibodies present in the sample, the lower the amount of free antigen, i.e., the amount of antigen that becomes bound to the second binding agent. Detection of the free antigen can be accomplished in numerous ways. In heterogeneous formats, the second binding agent is bound to a separable support, i.e., a suspendable or non-suspendable solid phase. For example, the second binding agent can be an anti-antigen antibody or a receptor such as streptavidin that can bind to a ligand that is bound to the antigen. In these formats the sample and the antigen are first combined and the first binding agent is then added. After addition of the second binding reagent bound to a support, the support is separated from the mixture. The amount of antigen that has become bound to the second binding agent-support can be measured directly or indirectly. When the antigen has a label bound to it, the presence of the label on the support can be detected. With certain supports, particularly indium, silica, and acoustic devices, even unlabeled antigen can be directly measured. Alternatively, the antigen can be indirectly measured by adding a reagent that will cause the antigen to be specifically labeled, e.g., by adding a labeling agent such as a labeled antibody to the antigen. The label can then be detected by methods well known to those skilled in the art.

Detection of antibodies is a useful tool in the diagnosis of infectious diseases. Detection of autoantibodies is also useful in the diagnosis of autoimmune disease. The above assay method can be used to detect numerous antibodies such as antibodies to human immunodeficiency virus ("HIV"), rubella or herpes and autoantibodies such as autoantibodies to insulin, to glutamic acid decarboxylase ("GAD"), both the 65 kd and the 67 kd isoforms but more particularly, $GAD_{65}$; and to other islet cell antigens.

There has been much research relating to detecting autoantibodies as a risk factor for patients developing insulin dependent diabetes mellitus ("IDDM"). There are several autoantibodies that are believed to be indicative of IDDM, which is also known as Type I Diabetes or juvenile diabetes. These include autoantibodies to pancreatic islet cell antigens such as insulin, and most recently autoantibodies to the 65 kd isoform of glutamic acid decarboxylase ("$GAD_{65}$") and IA-2. Autoantibodies to $GAD_{65}$ have been suggested to be one of the earliest markers for the development of IDDM. These autoantibodies are present several years before clinical onset of IDDM, at which time intervention steps could be taken to deter the progression of the disease.

Accordingly, an assay illustrative of the above method is the following. Recombinant $GAD_{65}$ is labeled with biotin to provide bGAD. This conjugate is then incubated with patient serum samples. A conjugate of protein-A and dextran aldehyde of the present invention is then added and the incubation continued. The suspension is transferred to a microtiter well that has been coated with streptavidin. After incubation to bind free bGAD, the well is washed and incubated with a mouse monoclonal antibody to GAD, which is either conjugated to a label such as horseradish peroxidase ("HRP") or unconjugated. When unconjugated antibodies are used, the well is washed again and then incubated with labeled anti-mouse IgG antibodies. In either case, after the labeled antibodies are added, the well is washed a final time and incubated with any additional sps members. For example, if the label is HRP, then the final incubation could include a solution containing hydrogen peroxide and tetramethylbenzidine, and color development would be read after incubation.

In an assay performed following this format in the present invention, samples that were known to be anti-$GAD_{65}$ negative showed minimal suppression in signal. Samples that were known to be anti-$GAD_{65}$ positive had suppressed color development.

The invention is demonstrated further by the following illustrative examples.

EXAMPLES

Parts and percentages herein are by weight unless otherwise indicated. Temperatures are in degrees Centigrade (° C.).

Example 1

Preparation of Protein A—Dextran Conjuqate

Materials and Equipment

Dextran T-500 from Pharmacia, catalog #17-0320-02.

Allyl glycidyl ether from Aldrich, catalog #A3,260-8.

Zinc tetrafluoroborate, $Zn(BF_4)_2$, 40 wt % solution from Aldrich, catalog #33,386-7.

Sodium hydroxide from Mallinckrodt AR (lot 7707 KMRT) was used to make 10M and 1.0M NaOH solution in water.

Dimethyl sulfide, $(CH_3)_2S$, was from Aldrich, catalog #M8,163-2.

1-Heptanol was obtained from Aldrich, catalog #H280-5.

Water (deionized) was obtained from a Millipore Filtration Unit.

UV-Vis Spectra were recorded on a Hewlett Packard 8452A diode array spectrophotometer.

Ozonator used was Polyozone Model T-816 Serial 3641 from Polymetrics, Colorado Springs, Colo.

Minikros Lab System (Microgon Inc. cat. #SYLS 121 01N) and Minikros tangential flow modules (M25S 300 01N, M25S 600 01N, M21M-300-01N) were also from Microgon Inc., Laguna Hills, Calif.

Oxygen (extra dry) used for generating ozone was obtained from Altair Gases and Equipment, San Ramon, Calif.

Sodium cyanoborohydride, $NaCNBH_3$ was from Aldrich Chemical Company (cat. #15,615-9).

Hydroxylamine hydrochloride, $NH_2OH.HCl$ was from Mallinckrodt (AR grade, lot #5258 KVEN).

Protein A was from Repligen Corporation (Product code 15001-10-00, product lot RC7151) supplied as 50 mg/mL solution in water.

Sodium Acetate, NaOAc, was from Mallinckrodt (AR grade, lot #7364 KPNJ) Acetate buffer, 0.1M, pH 5.0.

$^1$H-NMR and $^{13}$C-NMR spectra were run in $D_2O$ (from Aldrich, 99.5%) on Bruker WP-250 MHz Spectrometer. The $^1$H chemical shifts were recorded with water as the reference peak at 4.67 ppm. Acetone and Ethanol were used as internal reference in the $^{13}$C NMR spectrum, the anomeric carbon at 99.1 ppm was subsequently used as the reference peak.

Size exclusion Chromatography was performed on a Pharmacia FPLC system consisting of a LKB controller LCC 500 plus, two Pumps P-500 and an automated motor valve MV-7. The column used was Superose 6 HR 10/30 (Pharmacia catalog #17-537-01). The recorder used was a Pharmacia LKD Rec-102. The detector was a Waters Associates Differential Refractometer R401.

Lyophilization was performed on a 8 L VirTis Benchtop Freeze Dryer (Scientific Products).

1) Preparation of Dextran Aldehyde

Dextran (400 g, 500 kD) was dissolved in 1.5 L of water (Millipore), in a 4 L beaker by heating at 70° C. with overhead stirring. The dextran was added to water at 70° C. in 30–50 g portions, each portion being added after the first portion had dissolved. The overhead stirrer was set at 300–400 rpm.

The hot dextran solution was filtered through a fritted funnel (coarse) into an erlenmeyer flask and the filtered solution was poured into a 3-necked flask preequilibrated at 70° C. The beaker was rinsed with 50 mL of hot water, which was filtered through the fritted funnel into the erlenmeyer. This filtrate was added to the reaction mixture.

The funnel was removed from the side neck of the flask and a dual entry Claisen distillation adapter was inserted in its place. The overhead stirrer was started and set at 600–700 rpm and the temperature of the dextran solution was allowed to reach 70° C. The temperature of the oil bath was set at 72–75° C. The reaction was conducted under argon. The solution of $Zn(BF_4)_2$, (400 mL, 25 wt % in $H_2O$, pH 1.8±0.2) was poured into the flask containing the dextran solution using a funnel on the Claisen adapter. The funnel was removed from the Claisen adapter and replaced with an addition funnel (500 mL capacity) with a pressure equalizing side arm.

Allyl glycidyl ether (500 mL of the 1.5 L to be added) was added into the addition funnel (in 3×500 mL portions) at 8–10 mL/min, while the reaction temperature was maintained at 70±2° C. The addition of the allyl glycidyl was continued until all of the 1.5 L were added. Then, the temperature of the reaction mixture was increased to 80° C. The reaction was allowed to proceed for 12–13 h at 80° C. under argon, while being continuously stirred (600–700 rpm).

The reaction vessel was removed from the oil bath and the reaction mixture was allowed to cool to 30° C. The cooled reaction mixture was then poured into 6.0 L of water (Nalgene bucket with spigot) and stirred manually. The diluted reaction mixture was purified by ultrafiltration using a Microgon tangential flow diafiltration system. The allyloxy dextran was concentrated to 1.0–1.5 L.

An aliquot (50 mL) of the filtrate was removed and freeze dried for analytical purposes. The remaining solution of allyloxy dextran in water was stored at 4° C. and used for the next step. The $^1$H and $^{13}$C nuclear magnetic resonance (NMR) spectra of the above allyloxy dextran was consistent with the expected product.

The allyloxy dextran was subjected to ozonolysis in a 4.0 L beaker equipped with an overhead stirrer. The mixture was stirred at 300–350 rpm and allowed to attain room temperature. Ozone was generated by an ozonator and was added by means of a gas bubbler immersed into the solution of allyloxy dextran at a pressure of 9.0 psi and a flow rate of 2.0 LPM (liters per minute). Ten mL of heptanol was added as an antifoamer. The reaction was monitored by $^{13}$C-NMR; the disappearance of the olefinic resonances at 118 and 134 ppm was used as an indication for the completion of the reaction. The ozone addition was continued for 5–6 h. The reaction mixture was cooled to around 10° C. To this was added 50 mL of dimethyl sulfide and stirring under an argon atmosphere was continued for 10 h. The reaction mixture was allowed to attain room temperature while being stirred (300–350 rpm) over this time. The resulting dextran aldehyde was purified by Microgon ultrafiltration.

2) Conjugation of Protein A to Dextran Aldehyde

A 2 mg/mL solution of dextran aldehyde from above was prepared in 0.1M acetate buffer (pH 5±0.1) with heating at 65–70° C. The dextran aldehyde solution was cooled to ambient temperature (22–25° C.) and 1 mL of the protein A solution was added with stirring to the dextran aldehyde solution. The pH of the mixture was maintained at 5±0.1. A solution of sodium cyanoborohydride in water (63 mg/mL) and 200 μL of the solution was added to a stirring solution of protein A and dextran aldehyde. The reaction was stirred overnight (16–18 hours). A 1.0M solution of hydroxylamine in acetate buffer was prepared (pH 5.0) and 1.0 mL of this solution was added to the above reaction mixture. Stirring was continued for 3–4 hour at ambient temperature. The reaction mixture was purified in an Amicon centriprep-100 (MWCO 100 kD). The filtrates were analyzed for Protein A by recording the OD at 280 nm. The retentate after the first centrifugation was diluted with water and the tubes were subjected to centrifugation at 4 krpm for 30 minutes. The filtrates were again analyzed as described above. The above purification steps were repeated an additional eight times. The retentates were pooled together and dextran was determined by rotation and Protein A was determined by absorbance at $A_{280}$.

The conjugation of dextran aldehyde and Protein A was also carried out in a manner similar to that described above except that solid Protein A (500 mg vials from Repligen Corporation) was used in place of the commercial Protein A solution. The solid Protein A was dissolved in 10 mL of deionized water. Purification of the Protein A—Dextran conjugate was conducted by ultrafiltration using the Minikros Lab System from Microgon, Inc.

Example 2

Assay Utilizing a Protein A—Dextran Aldehyde Conjugate

| Abbreviations | |
|---|---|
| AET | 2-Aminoethylisothiouronium bromide |
| bGAD$_{65}$ | Biotinylated GAD |
| BSA | Bovine Serum Albumin |
| EDTA | Ethylenediaminetetraacetic acid |
| ELISA | Enzyme linked immunosorbent assay |
| GAD$_{65}$ | Human recombinat glutamic acid decarboxylase, molecular weight 65,300 |
| HRP | Horseradish peroxidase |
| IDDM | Insulin Dependent Diabetes Mellitus |
| MAb | Monoclonal antibody |
| PBS | Phosphate buffered saline |
| PLP | Pyridoxal-5'-phosphate |
| RIA | Radioimmunoassay |
| RT | Room temperature |
| SAV | Streptavidin |
| SDS-PAGE electrophoresis | Sodium dodecyl sulfate-polyacrylamide gel |
| TCEP | Tris (carboxyethyl) phosphine |
| TMB | 3,3',5,5'-Tetramethylbenzidine |

Preparation of Materials

Streptavidin-coated plates were made by standard techniques. The HRP-labeled anti-mouse antibodies were goat affinity purified antibodies to mouse IgG(γ-chain specific) (Kirkegaard & Perry Laboratories). All other chemicals were reagent grade and commercially available from sources such as Sigma and Fisher Chemical. All solutions were prepared in H$_2$O and all reactions were performed under ambient conditions unless otherwise stated.

Buffer Composition

The composition of the Reaction Buffer was as follows: 20 mM Tris, pH 7.4, 150 mM NaCl, 0.5% TRITON® X-100, 10 mM benzamidine (15.7 mg/10 ml), Pefabloc (Pentapharm) at 2.4 mg/10 ml, Aprotinin (Pentapharm, 229,500 KIU/ml) at 50 µl/10 ml, and Pepstatin A (Sigma) at 0.2 mg/10 ml.

Expression and Purification of Human Recombinant GAD$_{65}$

Baculovirus cells expressing recombinant human GAD$_{65}$ were grown in a fermentor and harvested. The pellet was lysed using a glass homogenizer. After disruption, the cell lysate was centrifuged and washed, and the washed pellet was extracted to obtain membrane-bound GAD$_{65}$. This membrane extract was then loaded onto a Q Sepharose column and eluted with a KCl gradient. Enzymatically active fractions were pooled and loaded onto a Phenyl Sepharose column. Elution was done by a reverse phosphate gradient. Eluted fractions were assayed for enzymatic activity and tested for purity on a 10% SDS-PAGE. Fractions with a purity near 95% by protein staining were pooled. The pool was concentrated using Centriprep-30 (Amicon). Concentrated GAD$_{65}$ was made 50% in glycerol and frozen at −70° C.

Iodination of GAD$_{65}$

The iodination protocol was based on the commercially available Enzymobead kit (BioRad) to yield [$^{125}$I]GAD$_{65}$. The contents of the single reaction vial, sold with the kit, was first rehydrated. To this rehydrated vial was added 2 µl (1 µg) purified GAD$_{65}$, 5 µl (0.5 mCi) $^{125}$I, 25 µl of 1% β-D-glucose, 50 µl 0.2 M sodium phosphate buffer pH 7.2, and 18 µl H$_2$O (total volume 150 µl), followed by incubation. After reaction with the Enzymobeads, the contents of the vial were loaded directly onto a size-exclusion gel column, and 200 µl fractions were eluted with PBS, 1 mM AET, and 1 mM PLP. Fractions containing 125I were identified by counting 1 µl aliquots.

Before use in the assay, [$^{125}$I]GAD$_{65}$ was preadsorbed using pooled normal human serum. 200 µl of [$^{125}$I]GAD$_{65}$ was mixed with 80 µl of Reaction Buffer, 100 µl of a pool of 8 IDDM negative control sera, and 20 µl of PBS. After an overnight incubation at 4° C., a 50% suspension of Protein A-Sepharose in PBS was added and incubated at 4° C. for 1 hr. This suspension was then subjected to microcentrifugation, the supernatant collected, the pellet washed with 400 µl PBS, and the two supernatants pooled and saved in aliquots at −70° C.

Biotinylation of GAD$_{65}$

Purified GAD$_{65}$, 282 µg/450 µl in GAD buffer, pH 7.0, was adjusted to a pH of between 8.0 and 8.2 using 1 µl of 6 N NaOH. The composition of the GAD buffer was 20 mL phosphate buffer (pH 6.8–7.0), 20 µM PLP, 1 mM AET, 1 mM EDTA, 0.1% TRITON X-100 and 10% glycerol. Then, 4 µl of 10 mM PLP and 5 µl of a 41 mg/ml solution of TCEP were added. After incubation on ice, biotinylation was carried out by adding 5 µl of iodoacetyl-LC-biotin (Pierce) for 3 hours at 4° C. in the dark. Unreacted biotin was separated by centrifugation. The biotin:GAD$_{65}$ ratio was determined to be approximately 3 to 5 mole biotin/mole GAD$_{65}$.

Mouse anti-GAD$_{65}$ Antibodies

Mice were immunized with GAD$_{65}$, expressed and purified as described above, and MAbs raised according to standard procedures such as described in Milstein and Kohler, supra.

The resulting monoclonal antibodies (MAbs) were tested in a standard ELISA format and the best MAbs were selected based upon specificity for GAD$_{65}$.

A mixture of six anti-GAD MAbs was used in early assays to detect bGAD$_{65}$ bound to SAV-coated plates, each MAb at 1 pmole/µl in PBS plus 0.2% sodium azide. The final concentration of each MAb was 0.2 pmol/100 µl/well.

Later assays utilized only one anti-GAD MAb, which was labeled with HRP, thus eliminating the need for the HRP-labeled anti-mouse MAbs.

Protein A-Sepharose Suspension

Protein A-Sepharose (CL-4B, Sigma Chemical Company) was made into a 50% suspension in PBS and 0.1% azide.

Protein A-Dextran

A conjugate of Protein A-dextran from Example 1 above was made into a phosphate buffered saline solution (BioWhittaker, Walkersville, Md.).

MICROTRAK® Plate Washer and Reader

The microtiter plate washer and reader are components of the MICROTRAK® EIA System (Syva Company). The wash solution used was the MICROTRAK Chlamydia EIA wash buffer: 0.559 g/ml trisodium citrate, 0.002 g/ml citric acid, 0.0182 ml/ml TWEEN® 20, 0.3175 ml/ml glycerol, pH 6.5–6.9. Each wash cycle was set for 300 µl/well×5.

Human Serum Samples

Human sera used in these experiments were either control samples (no autoantibodies to GAD$_{65}$) or from patients with IDDM (autoantibodies to GAD$_{65}$ present), which were provided by Dr. Noel Maclaren at the University of Florida.

A) Radioimmunoassay (RIA) for GAD$_{65}$

To measure [$^{125}$I]GAD$_{65}$ bound by human sera, an overnight incubation was set up at 4° C. containing 6 µl of human sera, 10 µl (approximately 150,000 cpm) [$^{125}$I]GAD$_{65}$ preadsorbed with negative human sera in Reaction Buffer in a total volume of 25 µl. After overnight incubation, 50 µl of 50% Protein A-Sepharose was added and the incubation continued with gently shaking for 1 hr at 4° C.

After Protein A-Sepharose incubation, the suspension was centrifuged at RT, washed 3× with 750 µl of ice cold 20 mM Tris, pH 7.4, 150 mM NaCl, 0.5% TRITON X-100. Each wash was counted in a gamma counter and the pellet was counted after the final wash.

The following table summarizes typical counts found in each of the 3 wash fractions or bound in the pellet with negative sera or positive sera:

| Serum | Total Counts | Wash 1 | Counts in Wash 2 | Wash 3 | Counts Bound |
|---|---|---|---|---|---|
| Negative | 188,037 | 140,940 | 12,280 | 2,236 | 2,130 |
| Positive | 196,063 | 118,324 | 12,804 | 4,536 | 11,230 |

Since the RIA uses an excess of radiolabeled material, a very small percentage of the input counts is finally obtained in the bound fraction. This is illustrated below, as the percent of radioactive GAD$_{65}$ that is bound:

| Serum | % Counts Bound |
|---|---|
| Negative | 1.1 |
| Positive | 5.7 |

The depletion assay of this example involves a reaction between antigen and antibodies and the subsequent detection of antigen not complexed with antibodies. It was expected that the amount of anti-antigen antibodies in a sample would be inversely correlated to the A$_{450}$ values in the depletion assay of this example. As a result, in this assay a sample is judged "positive" when the A$_{450}$ value is below the cutoff value determined by the mean, minus 2 or 3 standard deviations, of several normal, control sera. This is in contrast to the typical RIA where a sample with a cpm value higher than the control mean cpm+2 or 3 SDs is judged as "positive". This is best illustrated in the following assay.

B) Enzyme Immunoassay (EIA) for GAD$_{65}$ (without centrifugation)

25 µl human sera in BSA buffer (10 mM KPhos, pH 7.0, 1 mM AET, 1 mM EDTA, 20 µM PLP, 0.1% TRITON X-100, 10% glycerol and 1 mg/ml protease-free BSA) was mixed with 15 µl bGAD$_{65}$ (1.5 fmol per assay) and 10 µl 5× Reaction Buffer to a final volume of 50 µl. This was incubated for 2 hours at RT.

50 µl of Protein A-Dextran (1 to 25 dilution of stock in PBS) was added and incubated 1 hour at RT.

80 µl of supernatant fluid (containing unbound bGAD$_{65}$) was withdrawn and transferred to a prewashed SAV-coated plate. After incubation for 1 hour at RT, with shaking, the plate was washed on the MICROTRAK system.

100 µl of MAb(6G10)-HRP conjugate (1:320 dilution in Syva conjugate diluent, prewarmed at 37° C.) was added and incubated for 1 hour at RT, with shaking, followed by washing on the MICROTRAK system.

TMB substrate was added and developed at RT for 30 minutes. Color development was stopped with 1 N H$_2$SO$_4$ and read at 450 nm.

Seven out of nine patient sera were diagnosed correctly by this method. This is in contrast to conventional ELISA techniques which judged correctly only two out of the nine samples.

C) Comparison between EIA and RIA

In order to assess the analytical performance of the assay of the present invention, comparison was made with test sera previously assayed by the RIA method. The primary objective was to determine if results from the two methods would correlate, irrespective of the nature of the sera, i.e., control or patient samples with a range of GAD$_{65}$ autoantibody titers.

The assay protocol was as described above in B) with the following modifications: serum (24 µl), bGAD$_{65}$ (20 µl containing 12 fmol), 5× Reaction Buffer (20 µl) and deionized H$_2$O (36 µl) were incubated overnight at 4° C. Protein A-Sepharose (200 µl of a 50% suspension) was added and further incubated at 4° C. for 1 hour. This was then centrifuged for 2 minutes at RT. The supernatant (180 µl) was carefully collected and two aliquots of 90 µl each were added to two SAV coated wells in a plate to generate duplicate values. The rest of the protocol was as explained in B) above.

The resulting clinical data indicated excellent correlation between the results of the present assay and the data obtained from the RIA.

While the present invention has been described with reference to the specific embodiments thereof, it will be understood by and obvious to those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A polymer comprising a sequence of repeating monosaccharide units, each of which is independently selected from monosaccharide units of the formula:

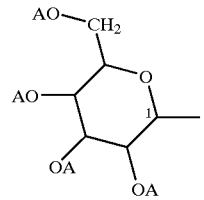

wherein one of the A's is a bond to the C1 glycosidic carbon of another of said units and the other A's are independently selected from the group consisting of H and QL, wherein L is a linking group linking O and Q and Q is C(Z)=D wherein D is O or CR$^1$R$^2$ wherein R$^1$ and R$^2$ are independently H, alkyl or aryl and Z is H or C(Y)=O wherein Y is R$^3$, OR$^3$ or NR$^3$R$^4$ wherein R$^3$ and R$^4$ are independently H, alkyl or aryl and wherein any of L, R$^1$, R$^2$, R$^3$ and R$^4$ may be taken together to form a ring with the proviso that at least two of the A's in said polymer are QL.

2. The polymer of claim 1 having from about 50 to 50,000 repeating monosaccharide units.

3. The polymer of claim 1 wherein Q is C(Z)=D wherein D is O and Z is H.

4. The polymer of claim 1 wherein Q is C(Z)=D wherein D is CR$^1$R$^2$ and Z is H.

5. The polymer of claim 1 wherein Q is C(Z)=D wherein D is O and Z is C(Y)=O wherein Y is OH.

6. The polymer of claim 1 wherein at least two of the A's are QL in at least one of said monosaccharide units for every 20 monosaccharides units of said polymer.

7. A compound comprising:

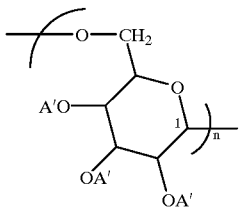

wherein n is 50 to 50,000, A's is independently selected from the group consisting of H and $Q^1L^1$, wherein $L^1$ is a linking group linking O and $Q^1$ and $Q^1$ is C(Z)=D wherein D is O or $CR^1R^2$ wherein $R^1$ and $R^2$ are independently H, alkyl or aryl and Z is H or C(Y)=O wherein Y is $R^3$, $OR^3$ or $NR^3R^4$ wherein $R^3$ and $R^4$ are independently H, alkyl or aryl and wherein any of L, $R^1$, $R^2$, $R^3$ and $R^4$ may be taken together to form a ring with the proviso that at least two of the A's in said compound are $Q^1L^1$.

8. The compound of claim 7 wherein $Q^1$ is C(Z)=D wherein D is O and Z is H.

9. The compound of claim 7 wherein $Q^1$ is C(Z)=D wherein D is $CR^1R^2$ and Z is H.

10. The compound of claim 7 wherein $Q^1$ is C(Z)=D wherein D is O and Z is C(Y)=O wherein Y is OH.

11. The compound of claim 7 wherein at least two of the $A^1$'s are $Q^1L^1$ in at least one of said monosaccharide-units for every 20 monosaccharides units of said compound.

* * * * *